United States Patent
Schneider et al.

(10) Patent No.: US 7,371,368 B2
(45) Date of Patent: *May 13, 2008

(54) ODOR CONTROL COMPOSITION AND PROCESS

(75) Inventors: David J. Schneider, Union, KY (US); Charles A Schneider, Villa Hills, KY (US)

(73) Assignee: Schneider Advanced Technologies, Inc., Union, KY (US)

( * ) Notice: Subject to any disclaimer, the term of this patent is extended or adjusted under 35 U.S.C. 154(b) by 561 days.

This patent is subject to a terminal disclaimer.

(21) Appl. No.: 10/855,704

(22) Filed: May 27, 2004

(65) Prior Publication Data

US 2004/0265265 A1 Dec. 30, 2004

Related U.S. Application Data

(63) Continuation-in-part of application No. 09/957,230, filed on Sep. 20, 2001, now Pat. No. 6,743,420.

(51) Int. Cl.
*A61L 9/00* (2006.01)
*A61L 9/01* (2006.01)

(52) U.S. Cl. .................................... 424/76.2
(58) Field of Classification Search ............... 424/76.2
See application file for complete search history.

(56) References Cited

U.S. PATENT DOCUMENTS

2002/0086039 A1 * 7/2002 Lee et al. .................... 424/401
2003/0162838 A1 * 8/2003 Yumioka et al. ............ 514/625

* cited by examiner

*Primary Examiner*—Shelley A. Dodson
(74) *Attorney, Agent, or Firm*—Richard M. Klein; Fay Sharpe LLP

(57) ABSTRACT

The disclosure of this invention relates to odor control and more particularly, to a process and composition whereby household, institutional and industrial odors are eliminated wherein these odors are incorporated in a variety of substrates or are emitted from industrial sludges, gas side streams, waste water, etc. The odor control composition of this invention is a solution containing active ingredients which will provide or demand active Cl+ donor which may incorporate a suitable wetting agent. The solutions in this invention may further be buffered. The concentration of the Cl+ donor can be from about 0.1 to about 15 weight percent when used. The concentration of the wetting agent can be from about 0.1 to about 5%. The solutions of this invention are effective over a pH range of about 6-14, with a preferred pH range being from 8 to about 9.5. Solutions in accordance with this invention may further incorporate an effective amount of a synergist.

8 Claims, No Drawings

ODOR CONTROL COMPOSITION AND PROCESS

RELATED APPLICATIONS

This application is a continuation in part application of application Ser. No.09/957,230 filed Sep. 20, 2001 now U.S. Pat. No. 6,743,420.

FIELD OF THE INVENTION

This invention is concerned with odor control technology and more particularly with household, institutional and industrial odor control. In accordance with this invention, odors attributed to a wide variety of human, animal and industrial endeavors can be controlled or eliminated. The odor control process of this invention comprises the application of a solution, of the odor control composition of this invention, to an odor containing substrates, and/or industrial waste products.

BACKGROUND OF THE INVENTION

The application of materials and solutions to substrates for purposes of odor control is common and in fact is thousands of years old, in the most common situation solutions or materials with a pleasant odor are applied to a substrate, for example, to furniture or carpets. In the past the most common method of odor control was to apply solutions which are perfumes to the odor containing substrate. These perfumes did not control the odor but only masked the odor. That is in the prior art the odor was not controlled but instead it was only masked. In contrast in accordance with the subject invention the troublesome odors are not just masked but instead they are chemically controlled or eliminated. This end is effected by treating the substrate with a solution which contains Chloramine-T, Chloramine-B or N-Chloro-4-Carboxybenzenesulfonamide sodium salt. With this invention it is possible to eliminate odors resulting from a wide range of sources such as smoking, animal and human fluids, cat litter, mildew, cooking, industrial by products etc. In its broadest terms, this invention relates to the utilization of solutions of Chloramine T, Chloramine-B and N-Chloro-4-Carboxybenzenesulfonamide sodium salt, which react with odor producing molecules as may be contained in a substrate or in an industrial waste product. The performance of the odor control compositions in accordance with this invention, is further enhanced by the presence of small percentages of a low molecular weight alcohol.

BRIEF DESCRIPTION OF THE INVENTION

Odor control has been a problem which man has addressed for thousands of years, scented or perfumed compositions for odor control are well known in the prior art. Regardless of the widespread usage of these compositions, the problem of effective odor control remains a common and troublesome problem. This situation results from the fact that the prior art solutions do not control the odorous materials as may be in a substrate or part of an industrial waste product. In contrast the compositions of this invention reacts with the odorous materials as are contained in a substrate or industrial byproduct and thereby eliminate the same.

The subject invention is concerned with a means whereby undesirable odors can be eliminated by providing a latent source of the active chlorine and an active nitrogen sulfonamide produced by Chloramine-T, Chloramine-B or N-Chloro-4-carboxybenzeinesulfonamide to react with the odorous material on a molecular level.

Herein after Chloramine T will be referred to as CHT and N-Chloro-4-Carboxybenzeinesulfonamide will be referred to as CH-BENZ and Chloramine B will be referred to as CHB.

In the preferred embodiment, the odor controlling solution for use in this invention incorporates CHT, and/or CH-BENZ a wetting agent and a buffering agent. By using the composition and process of this invention odors in the substrate are eliminated because the odor controlling solution wets out the substrate thereby allowing the active chlorine moiety and the active nitrogen of the sulfonamide moiety backbone to react with the odorous molecules. The odor controlling composition comprises solutions of CHT and CH-BENZ which may contain a compatible wetting agent. The wetting agent must not degrade the active chlorine in the CHT or CH-BENZ. Preferred wetting agents are generally anionic. In other words the wetting agent in the odor control solution of this invention should not degrade the active Cl+ moiety or the backbone moiety which is formed when CHT or CH-BENZ goes into solution. If the Cl+ moiety is degraded the CHT and CH-BENZ are less effective as an odor control agent.

DESCRIPTION OF THE PREFERRED EMBODIMENT

In accordance with the above discussion this invention is concerned with a process for controlling odors in household, institutional and industrial applications. Perfumed odor control compositions have been used for thousands of years however these solutions did not destroy the odorous materials but instead they only masked the odors caused by the odorous materials. In contrast to this masking of the troublesome odorous material in the prior art, the compositions of this invention react with the odorous molecules. In the prior art odor control compositions, are perfumes wherein the odors are masked with a synthetic or natural essence . In the subject invention, instead of masking the odor with a perfume, the odor causing molecules are degraded by reaction with the Cl+ moiety and with the chemical moiety which remains after the Cl+ moiety is removed from CHT or CH-BENZ. The use of Cl+ is common in odor control, the most common Cl+ producing composition is household bleach. The preferred sources of the Cl+ moiety for use in accordance with this invention are Chloramine-T and CH-BENZ.

The preferred Chloramine-T for use in this invention is a tri hydrated sodium salt having the following formula.

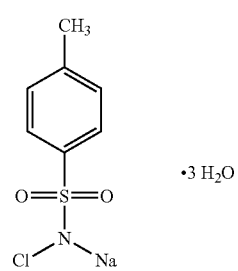

Herein after Chloramine T will be referred to as CHT. For use in this invention the Cl+ cation produced by N-Chloro- 4-Carboxybenzeinesulfonamide is also useful. Hereinafter N-Chloro-4-Carboxybenzinesulfonamid will be referred to as CH-BENZ. As is mentioned above bleach has been commonly used as a source of Cl+ cations which are useful as deodorizers. Because of the problems associated with the use of bleach, i.e. the discoloration of the substrate, and because it does not contain an active type nitrogen sulfonamide, it is generally not suitable for use as a deodorizer. In addition the Cl+ cation which is produced by bleach is much more ionic when compared to the Cl+ cations produced by CHT or CH-BENZ. That is when compared to the Cl+ cations produced by bleach the Cl+ cations produced by CHT and CH-BENZ are much more covalent and less ionic. As a result of this covalence the side effects produced by the Cl+ cations produced by CHT and CH-BENZ are not as severe as those produced by bleach and therefore is generally only available on demand. As a result the Cl+ cations produced by CHT and CH-BENZ can be used to deodorize as it does not have undesirable side effects i.e. a strong bleach smell, the undesirable bleaching of the odor containing substrate etc. Further CHT and CH-BENZ are more stable than bleach and have a higher Cl+ activity.

When compared to bleach CHT and CH-BENZ are a superior deodorizing agents as the chemical moiety, the backbone, remaining after the Cl+ cation is released by CHT and CH-BENZ, further react with the odor containing molecule thereby permanently removing it as a potential source of odor. In contrast the chemical moiety which remains after the Cl+ cation is removed from bleach has no ability to react with odor causing molecules.

Most odor causing molecules are mercaptans, sulfides or amine based compounds, or other sulfur or nitrogen compounds. CHT and CH-BENZ are excellent agents for eliminating odors which are mercaptan, sulfide or amine based as both the Cl+ cation produced by CHT and CH-BENZ and the residual chemical moiety remaining after the Cl+ cation is produced, reacts with the odor causing molecule.

In order for CHT and CH-BENZ to be effective they must come into contact with the substance which is responsible for the odor. If the substance which is responsible for the odor is in an environment which makes access difficult i.e. pet stains in a carpet, a means must be provided for bringing the CHT and CH-BENZ into contact with the odor causing substance. In many instances when aqueous solution is used as the delivery medium the solution tends to bead up on the substrate. Therefore, when the water component of the solution evaporates the substance in solution is deposited only in localized areas. In the case at hand if an aqueous solution of CHT or CH-BENZ were applied to a carpet containing pet stains, the solution would bead up on the carpet, such that when the water evaporated the placement of the CHT or CH-BENZ on the carpet would be spotty. Due to this poor placement the two reactive components of the CHT and CH-BENZ would not be in position to totally react with the odor causing substance on a molecular basis. That is the reaction of the CHT or CH-BENZ with the pet stain would be incomplete, and hence the odor control would be incomplete.

While CHT and CH-BENZ are the preferred compounds for use in accordance with this invention Chloramine-B hereinafter CHB may also be used, the formula for Chloramines-B is as follows;

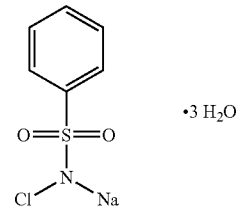

Further the formula for CH-BENZ is as follows;

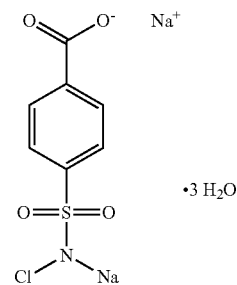

The use of wetting agents with various solutions in order to reduce surface tension is common in the prior art. For example wetting agents are commonly added to herbical solutions to allow the herbicide to wet out plant leaves Likewise the use of wetting agents with insecticides is common.

In accordance with one embodiment of this invention a substance is added to the CHT and CH-BENZ solutions to reduce the surface tension of these solutions. As is discussed above CHT and CH-BENZ function by the reaction of the Cl+ moiety with the odor causing molecule. In part, this invention is concerned with the fact that many substances which are suitable for reducing the surface tension of the solution adversely affect the formation of the Cl+ moiety, from CHT or CH-BENZ or degrade said Cl+ moiety once it is formed.

Suitable substances which are useful in accordance with one embodiment of this invention for reducing the surface tension of the CHT and CH-BENZ solutions, are synthetic and natural wetting agents. Wetting agents are generally classified as cationic, anionic, amphoteric and nonionic. Because there are thousands of natural and synthetic wetting agents it is impossible to make generalizations as to which would be effective in the composition of this invention. With this caveat it can be said that generally the most preferred wetting agents for use in accordance with this embodiment of this invention are anionic wetting agents, with the next preferred class of wetting agent being a nonionic wetting agents.

Amphoteric and cationic wetting agents are least preferred for use with the wetting agent embodiment of this invention.

Regardless of the above comments satisfactory wetting agents may be found in any class of wetting agents.

While the applicant is not sure of all ramifications of how different wetting agents degrade the Cl+ moiety it is felt that functional groups such as alkenes, alcohol, ketone, phenols as may be contained on the base wetting agent molecule are particularly harmful to the Cl+ moiety. Further while it is impossible for the applicant to explore all the ramifications thereof, impurities as may be contained in various commercially available wetting agents can play a significant part in the degradation of the Cl+ moiety. Impurities which are known to facilitate the degradation of the Cl+ moiety are aromatic and conjugated phenols.

It has been found that the odor control properties of the Cl+ moiety produced by CHT and CH-BENZ can be enhanced by incorporating small percentages of select low molecular weight, short chain alcohol into the odor control compositions of this invention. Examples of suitable alcohols for this purpose are methanol, isopropanol and t-butanol. The applicant is not sure how these alcohol additions enhance the odor control properties of the Cl+ moiety, and the residual moiety. Because they contain a molecular combination of hydrophilic/hydrophobic ends, they can enhance exposure to the odor causing molecule.

Preferred alcohols for use as synergist are methanol isopropanol and t-butanol. The concentration of these alcohol synergist can be from about 0.01 to about 5% a more preferred range is from about 0.01 to about 3% with a most preferred range being from about 0.15 to about 1.5% and a most preferred concentration being about 0.25%.

Alcohol based synergist are advantageous because of the combined molecular hydrophilic/hydrophobic ends. The hydrophilic/hydrophobic ends of these additives facilitate the mixing of the various components of the odor control compositions of this invention. That is the synergist as set forth above have a polar component which will mix with polar additives. Further the synergist described above have a non polar component which will mix with non polar additives.

Synergist for use in the odor control compositions of this invention can also be used to control the evaporation rate of the odor control composition.

Further when t-butanol is used as a synergist it imparts a plesant odor to the odor control compositions of this invention.

The concentration of the wetting agent used in accordance with this invention can be from about 0.01 to 5%. A more preferred concentration for the wetting agent is from about 0.02 to about 1.5%. In order to achieve maximum efficiency in the odor control process the surface tension of the solution must be reduced so that CHT and CH-BENZ can reach and react with the odor causing molecules.

A factor in choosing the concentration of the wetting agent is the degree to which it foams. If undesirable foaming occurs anti foamers may be added to the solution.

For stability and for optimum performance as an odor killing agent the pH of the CHT and CH-BENZ solution should be between 7-14, with a more preferred pH range being between 7-9.5 with a most preferred range being between 8-9.

As is discussed above the pH range for CHT and CH-BENZ solutions for use in this invention can be from about 6-14. Below a pH of 6 CHT and CH-BENZ tend to decompose due to the acidic nature of the medium. While the solutions of this invention are effective above a pH of 10.0, solutions having a pH of 10.0 can only be used for industrial applications, due to their caustic nature.

Solutions for use in this invention exhibit excellent stability at a pH range of 8-9.5. This stability is important in domestic applications of this invention where long shelf life is very desirable.

A 5% solution of CHT or CH-BENZ naturally buffers itself at a range of about 8.5-9.5. In order to maintain the CHT and CH-BENZ in solutions at these pH ranges it is preferred that the CHT and CH-BENZ solutions be buffered.

The buffering of the CHT and CH-BENZ solutions further compensate for any change in pH that may result from the acidity of the water which is used to make the solution, the conditions of application, the type of substrate, or industrial waste and the nature of the odor causing molecule.

Buffering agents which are suitable for use in accordance with this invention are sodium bicarbonate, potassium bicarbonate, sodium carbonate, potassium carbonate, acetate buffers (such as sodium acetate), phosphate buffers (such as tri and di sodium phosphate and mixtures thereof, pH blended phosphates, sulfate buffers (such as di and tri sodium sulfate and mixtures thereof.

Because of price, ease of use, low toxicity and their effect on the environment, the above listed sodium and potassium bicarbonate are preferred buffering agents for use in this invention. Buffered solutions are advantageous in that the active ingredients of the odor control solution of this invention can be shipped in powdered form and mixed by the consumer with no adverse effects.

The concentration of the buffer can be from 0% up to the limit of solubility. The preferred range for the concentration of the buffering agent is from about 5% to about 200% of the CHT or CH-BENZ in solution. A more preferred range is from about 5% to about 50% with a most preferred concentration being 25-50%.

CHT has a limit of solubility of about 15% at room temperature in water. CH-BENZ has a limit of solubility of about 20% at room temperature in water. However, for shipping in North America it is preferred that the concentration be 10% or less in order to prevent the CHT and CH-BENZ from coming out of solution during transport.

For the industrial odor control it is preferred that the concentration of CHT and CH-BENZ be about 5-10%. For residential consumer use the concentration of CHT and CH-BENZ can be from about 0.1 to about 2.0%, with a more preferred range being from about 0.5 to about 1.0% percent, with the most preferred concentration being 0.75%. These lower concentrations keep the bleach like smell to a minimum but still give the desired odor control.

For use in this invention CHT, CHB and CH-BENZ are effective odor control agents, mixtures of these odor control agents may be utilized. Further these odor control compositions may contain trace amounts of fragrances, usually less than 1% by weight.

The composition and process of this invention is suitable for use in controlling the odor which is emitted from a wide variety of industrial sludge such as sewerage treatment sludges, paper making sludges, waste from animal grow outs, animal processing and animal habitats etc.

This invention is particularly suited into the treatment of the sludges which is the byproduct of paper making and in particular the Kraft paper making process.

Chloramine-T is the preferred source of the Cl+ moiety for use in odor control in conjunction with Kraft paper byproducts. As is discussed above, another suitable source the Cl+ moiety are CHB and CH-BENZ.

Paper mills are notorious for creating foul odors. In particular the Kraft paper making process produces an odor which is often categorized as a rotten egg smell. In the past society was tolerant of these odors as society often took the position that the smell of a paper mill was the smell of money. The odor of a paper mill is primarily based on odorous mercaptans which the human nose can detect at concentrations which approach one part per billion. These paper mill odors can originate from the holding ponds which are used to hold the sludge which is a byproduct of the paper making process, or from the sludge which results from the treatment of the paper mill stack gases or from solid press. Odors originating with paper mills can often be detected by humans at distances which can exceed twenty miles.

While in the past society was tolerant of these odors in recent times society has become much less tolerant therefore it is important that these odors be eliminated.

The process and composition of this invention is particularly suited to eliminating paper mill odors due to the ability of CHT and CH-BENZ to react with mercaptans.

In accordance with the broadest aspects of the paper mill sludge segment of this invention paper mill sludge can be treated with solution of CHT or CH-BENZ.

The preferred solvent is water, however, other solvents can be used. The solution which are used to treat Kraft paper mill sludge can have a concentration of CHT or CH-BENZ from about 3 to about 5 percent with a more preferred range being from about 5 to about 12 percent with a most preferred concentration being 8 percent. All concentrations listed in this application are by weight.

For treating paper mill sludge the preferred solution for use in this invention is an aqueous solution of CHT or CH-BENZ which is buffered to a pH of about 9.

While a wide variety of buffering agents can be used the preferred buffering agents for use in Kraft paper odor control are potassium and sodium bicarbonate.

Further for Kraft paper odor control the solutions of CHT or CH-BENZ may incorporate a wetting agent, it is preferred that the solution incorporate a nonionic wetting agent at a concentration of from about 0.01 to about 5 percent. The caveats and qualifications for wetting agents as are discussed above likewise apply for the treatment of paper mill sludges. The preferred wetting agent for use in conjunction with paper mill sludge treating compositions is an anionic wetting agent sold under the trademark Avanel S-74 by the BASF Chemical Co. of Mt. Olive N.J. The applicant believes that Avanel S-74 is Ethoxylated ROH sulfonate., where R is $CH_3$, $CH_3$ $CH_2$ or $CH_3$ $CH_2$ $CH_2$.

The preferred composition for use in treating paper mill sludges is in accordance with Table 1.

TABLE I

| | |
|---|---|
| Chloramine T | 8% |
| Buffering Agent | Sodium Bicarbonate 2% |
| Wetting Agent | 0.5% |

In addition to treating paper mill sludge with solutions of CHT and/or CH-BENZ in accordance with the above description these sludges can be treated by dusting the same with powdered CHT or CH-BENZ. One skilled in the art recognizes this dusting must be done in such a manner as to achieve the proper concentration of CHT or CH-BENZ in the sludge.

In the dusting aspect of this invention the CHT and CH-BENZ go into solution in the aqueous component of the sludge which is being treated.

EXAMPLES

The present invention is illustrated by the following Examples which are not to be construed as limiting the invention to their details.

1. After a fire the air transfer ducts in a building were contaminated with a strong smoke odor which was transferred to air moving through the duct work. The building occupants found the smell of the air to be objectionable. The inside of the duct work was treated with an aqueous solution containing 0.75% CHT and 0.5% of dodecylbenzene sulfonic acid. The treatment was affected by atomizing the solution directly into the cold air return ducts. The furnace fan was then activated in order to spread the atomized solution throughout the duct work. In thirty minutes the smoke odor was eliminated.

2. The locker room, showers and workout areas of a health club smelled of human perspiration. These odors had proved to be impossible to eliminate using prior art odor control solutions. The solution of Example 1 was misted throughout the odorous area at a height of about 6 ft. above floor level. The perspiration odors were eliminated in a matter of minutes.

3. The inside of a used automobile had a strong tobacco smoke odor as a result of the previous owners smoking. After the automobile was traded in, the used car department of the automobile dealer tried to eliminate the smoke odor by spraying the inside of the automobile with an orange scented solution, in an attempt to mask the smoke odor. A subsequent owner of the automobile found the orange-tobacco smoke odor, which permeated the inside of the car to be objectionable. The whole inside of the car was sprayed with the solution of Example 1, as a result of this spraying the orange-tobacco smoke odor on the inside of the car was eliminated in approximately thirty minutes.

4. The carpet in the salad bar area of a restaurant emitted a strong, old or rotten, food odor. The carpet was vacuumed and the solution of Example 1 was applied to the area with a spray mist bottle. The odors were eliminated and did not return.

5. The inside of a mobile home which had been left closed for a considerable period of time had a stale odor. The inside of the mobile home was sprayed with the solution of Example 1. The stale smell was totally eliminated in about one hour .

6. A carpet cleaning company encountered a problem piece of carpet which exhibited the strong smell of cat urine. The carpet was sprayed with the solution of Example 1 and allowed to sit. The carpet was then cleaned and sprayed again with the solution of Example 1. The cat urine odor was eliminated and it did not return.

7. A skunk entered a residential basement and contaminated a basement and the furniture therein. The entire basement and the furniture was sprayed with the solution of Example 1. After thirty minutes the odor was gone.

8. Camping bedding gear was accidentally contaminated with motor oil. The bedding gear was washed however after washing the strong smell of motor oil persisted. The bedding gear was sprayed with the solution of Example 1. After approximately twenty minutes the motor oil smell was gone.

9. A zoo at a major city suffered major fire damage to a pavilion and an adjacent lodge. The adjacent areas were permeated with smoke and exhibited a strong smoke odor. The adjacent area including the floors, walls ceilings, furniture etc were sprayed with the composition of Example 1, except that the concentration of CHT was 1.25% and the concentration of the wetting agent was 1.00%. After a period of one hour the smoke odor was gone.

10. A paper mill press full of sludge was sprayed with 10 gallons of a solution having the following composition.

CHT -8%

Sodium Bicarbonate 1.5%

Avanel S-74 0.5%

Prior to spraying, the area was deemed to be a "high sulfide day" by an experienced workman. After spraying, the area was deemed to be a "very low sulfide day".

11. A carpet sample with synthetic fibers was sprayed with red fox urine which is sold by the Wildlife Research Center of Anaka, Minn. The urine is very pungent and is normally used to mask human odors in hunting and trapping endeavors. After spraying with the red fox urine the carpet sample exhibited a strong offensive odor. The sample was they sprayed with a water solution of 0.80% CHT and 0.03% of the above described Avanel S-74 anionic wetting agent. The solution was buffered with 0.118% sodium bicarbonate. The solution was then adjusted to a pH of 6.0 with a dilute solution of acetic acid. Within one minute of treating the carpet sample the offensive odor of the red fox urine was mitigated and the odor essentially eliminated over the next 24 hrs. and remained eliminated after five days.

12. A carpet sample with synthetic fibers was sprayed with red fox urine is sold by the Wildlife Research Center of Anaka, Minn. The urine is very pungent and is normally used to mask human odors in hunting and trapping endeavors.

After spraying with the red fox urine the carpet sample exhibited a strong offensive odor. The sample was then sprayed with a water solution of 0.80% CHT and 0.03% of the above discarded Avanel S-74 anionic wetting agent. The solution was buffered with 0.118% to sodium bicarbonate. The solution was then adjusted to a pH of 11.3 with a dilute solution of sodium hydroxide. Within one minute of treating the carpet sample the offensive odor of the red fox urine was mitigated and the odor essentially eliminated over the next 24 hrs and remained eliminated after five days.

Examples 13-20 demonstrate how the odor control properties of the Cl+ moiety as produced by CH BENZ, is the presence of t-butanol.

13. Fox urine was sprayed onto sand, a hard laboratory top and a clay surface wherein the clay sold under the trademark ZEOLITE. The three surfaces were then treated with an odor control agent which is sold under the trademark NATURES MIRACLE. In all three instances the odor control agent had no affect on the odor produced by the fox urine.

14. The surfaces as are set forth in Example 13 were sprayed with fox urine and immediately treated with an odor control composition comprising a mix of 0.15% CHT and 0.60% CH-BENZ was formulated with 0.25% t-butanol, Avenel S-74 surfactant 0.03%, and 0.2% sodium bicarbonate. To this was added a light floral fragrance. Immediately after spraying with the odor control composition the odors were controlled and did not return after a period of days. On all three surfaces the formulation had immediate and final efficacy to the fox urine odor.

15. The treated surfaces as are set forth in Example 13 were further treated with the odor control composition as is set forth in Example 14, except that the odor control composition did not incorporate the 0.25% to t-butanol. On all three surfaces the odor of the fox urine was reduced however, the odor control reduction was not as effective as the treatment in accordance with Example 14.

16. Two cat litter boxes were placed side by side. One litter box was treated with five sprays of the formulation as is set forth in Example 14 and one litter box was untreated. Several cats were allowed to use the litter boxes. Over a period of three weeks, on a weekly basis, the treated litter box was treated with 5 sprays. Over the three weeks test period the treated litter box had no odor while the untreated litter box had a strong ammonia and urine smell. Further, the cats exhibited a strong preference for the treated litter box.

17. A diaper pail was sprayed with the formulation of Example 14. The offensive diaper odor was eliminated.

18. A riding jacket that had been worn for equestrian events smelled of the barn and horses from weeks of riding. The jacket was sprayed with the composition as set forth in Example 14, the odors were eliminated.

19. Costumes used by professional actors on the New York stage were sprayed. It is difficult to wash costumes of this nature due to time constraints and because of the material be unsuitable for standard washing practices. Upon spraying the costumes the odors of human perspiration and body odors were eliminated.

20. During a house renovation it was found that dogs had urinated on the carpets and had urine seeped into the sub floor. The carpets were removed, the sub floor was spot sprayed, with the composition of Example 14, where the sub floor was strained. The floor was left to dry for one hour. The odor was gone. New carpet and pad were installed and the odor did not return.

In summary, the date of Examples 1 through 12 demonstrates that by use of the odor control composition and process of the subject invention, many common odors can be eliminated. Examples 13-20 illustrate how these odor control properties can be enhanced by the addition of small percentages of a low molecular weight alcohol to solutions of CHT and CH-BENZ.

The foregoing constitutes a description of various features of a preferred embodiment. Many changes to the preferred embodiment are possible without departing from the spirit and scope of the invention. Therefore, the scope of this invention should be determined with reference not to the preferred embodiment but to the following claims.

What is claimed is:

1. A process for controlling odor which is being emitted by a material which incorporates an odorous substance, comprising:
    applying a solution containing an effective amount of a Cl+ donor selected from the group consisting of Chloramine B and N-chloro-4-carboxybenzenesulfonamide to the material;
    wherein the solution has a pH of from about 6 to about 14 and further comprises an effective amount of low molecular weight alcohol.

2. The process of claim 1, wherein the concentration of the Cl+ donor is from about 0.1 to about 10 weight percent.

3. The process of claim 1, wherein the solution is buffered to a pH of from about 8 to about 9.5.

4. The process of claim 1, wherein the solution is buffered with sodium bicarbonate.

5. The process of claim 1, wherein the solution further contains a small percentage of a fragrance.

6. The process of claim 1, wherein the low molecular weight alcohol is t-butanol.

7. The process of claim 1, wherein the solution further incorporates an effective amount of a wetting agent which essentially does not react with the Cl+ donor.

8. The process of claim 7, wherein the wetting agent is an anionic or nonionic wetting agent.

* * * * *